(12) United States Patent
Champie

(10) Patent No.: US 11,179,350 B2
(45) Date of Patent: *Nov. 23, 2021

(54) NUTRACEUTICAL COMPOSITIONS COMPRISING C60 AND COX-2 INHIBITOR

(71) Applicant: Max Champie, Buena Vista, CO (US)

(72) Inventor: Max Champie, Buena Vista, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/220,890

(22) Filed: Dec. 14, 2018

(65) Prior Publication Data

US 2020/0188331 A1    Jun. 18, 2020

(51) Int. Cl.
| | | |
|---|---|---|
| *A61K 31/122* | (2006.01) | |
| *A61P 39/00* | (2006.01) | |
| *A61K 36/71* | (2006.01) | |
| *A61K 31/015* | (2006.01) | |
| *A61K 33/44* | (2006.01) | |
| *A61K 9/00* | (2006.01) | |

(52) U.S. Cl.
CPC .......... *A61K 31/122* (2013.01); *A61K 31/015* (2013.01); *A61K 33/44* (2013.01); *A61K 36/71* (2013.01); *A61P 39/00* (2018.01); *A61K 9/0053* (2013.01)

(58) Field of Classification Search
CPC ....... A61K 36/71; A61K 31/015; A61K 33/44
See application file for complete search history.

(56) References Cited

U.S. PATENT DOCUMENTS

| | | | |
|---|---|---|---|
| 6,777,445 B2 * | 8/2004 | Lei | A61K 31/015 514/557 |
| 2004/0009200 A1 | 1/2004 | Seyler | |
| 2010/0179103 A1 | 7/2010 | Desai | |
| 2011/0293588 A1 | 12/2011 | McCleary | |
| 2014/0140985 A1 | 5/2014 | Moussa et al. | |
| 2014/0308219 A1 * | 10/2014 | Ibrahim | A61K 8/97 424/58 |
| 2017/0258917 A1 * | 9/2017 | Subbiah | A61K 31/337 |
| 2018/0007935 A1 * | 1/2018 | Reh | A23L 2/66 |
| 2018/0008629 A1 | 1/2018 | Dixit | |
| 2018/0271906 A1 | 9/2018 | Moussa et al. | |
| 2019/0231670 A1 | 8/2019 | Pujos | |
| 2020/0054061 A1 | 2/2020 | Dischler | |

FOREIGN PATENT DOCUMENTS

| | | |
|---|---|---|
| CN | 109820739 A | 5/2019 |
| WO | 2015086239 A1 | 6/2015 |
| WO | WO 2016/090020 * | 6/2016 |

OTHER PUBLICATIONS

Elmowafy et al. Enhancement of Bioavailability and Pharmacodynamic Effects of Thymoquinone via Nanostructured Lipid Carrier (NLC) Formulation. AAPS PharmSciTech, vol. 17, No. 3, Jun. 2016.*
Tolba et al. Caffeic acid phenethyl ester, a promising component of propolis with a plethora of biological activities: a review of this anti-inflammatory, neuroprotective, hepatoprotective and cardioprotective effects. IUBMB Life, 65(8): 699-709, 2013.*
Stuchlik et al. Lipid-based vehicle for oral drug delivery. Biomed. Papers, 145(2), 17-26, 2001.*
Surh et al. Resveratrol, an antioxidant present in red wine, induces apoptosis in human promyelocytic leukemia (HL-60) cells. Cancer Letters, 140, 1999, 1-10.*
Prylutska et al. Complex of C60 fullerene with doxorubicin as a promising agent in antitumor therapy. Nanoscale Research Letters, 2015, 10: 499.*
Marsik et al. "In vitro Inhibitory Effects of Thymol and Quinones of Nigella sativa Seeds on Cyclooxygenase-1- and -2-Catalyzed Prostaglandin E2 Biosynthesis" Planta Med 2005, 71, 739-742.*
Ahmad et al. "A review on therapeutic potential of Nigella sativa: A miracle herb" Asian Pac J Trop Biomed, 2013, 3(5): 337-352.*
Gafner et al. ("Biologic evaluation of curcumin and structural derivatives in cancer chemoprevention model systems" Phytochemistry 65, 2004, 2849-2859).*
More et al. ("Intensified synthesis of structured lipids from oleic acid rich moringa oil in the presence of supercritical CO2" Food and Bioproducts Processing, 112, 2018, 86-95).*
Alam et al., "Development and evaluation of thymoquinone-encapsulated chitosan nanoparticles for nose-to-brain targeting: a pharmacoscintigraphic study," International Journal of Nanomedicine 2012:7 5705-5718.
Leone, Alessandro, "Moringa oleifera Seeds and Oil: Characteristics and Uses for Human Health" Int. J. Mol. Sci. 2016, 17(12), 1-14.
Gupta, Bhanushree, "Thymoquinone" Nutraceuticals, 2016, 1-9.
CN106692189A Translation, Dec. 19, 2019, 1-17.
Sayin, Volkan; et al. "Antioxidants accelerate lung cancer progression in mice," Sc Transl Med. 2014. 2 pages.
Moyer, Melinda Wenner, "Antioxidants may make cancer worse," Scientific American, Oct. 7, 2015. 7 pages.
Cha, Ariana Eunjung, "The latest study about antioxidants is terrifying. Scientists think they may boost cancer cells to spread faster," The Washington Post, Oct. 16, 2015. 3 pages.
Decker, Carrie, "Antioxidant therapies: A contraindication for melanoma?," AHC Media: Continuing Medical Education Publishing. Jan. 18, 2016. 10 pages.
Le Gal Beneroso, Kristell; "Antioxidant supplements linked to skin cancer and lung cancer growth," University of Gothemburg, Sweden, 2019. 2 pages.
"Antioxidants and Cancer—Should I take them?" Care Oncology US, Jun. 27, 2019. 6 pages.
A. Zaoui, et al; "Acute and chronic toxicity of Nigella sativa fixed oil," Phytomedicine, vol. 9, Issue 1, 2 pages.

(Continued)

*Primary Examiner* — Kortney L. Klinkel
(74) *Attorney, Agent, or Firm* — Fish IP Law, LLP

(57) ABSTRACT

An anti-inflammatory and anti-oxidative nutraceutical composition containing C60 fullerene, a COX-2 inhibitor, and a medium chain triglyceride. The combined use of C60 and COX-2 inhibitor has unexpected benefits in promoting health, including synergistic effects in fighting cancer, slowing aging, and in some cases, reversing aging. Advantageously, *Nigella sativa* ("black seed") oil is used to provide both medium chain triglycerides and COX-2 inhibitors.

11 Claims, No Drawings

(56) References Cited

OTHER PUBLICATIONS

Yanyan Liu; et al. "Inhibition of thrombin by functionalized C nanoparticles revealed via in vitro assays and in silico studies," Journal of Environmental Sciences, vol. 63, Jan. 2018. 3 pages.

Martinez EE, Anderson PD, Logan M, Abdulkadir SA (2012) Antioxidant Treatment Promotes Prostate Epithelial Proliferation in Nkx3.1 Mutant Mice. PLoS One 7(10): e46792. doi:10.1371/journal.pone.0046792. 12 pages.

Syeda Tasneem Towhid; et al. "Thymoquinone-induced platelet apoptosisapoptosis," Journal of Cellular Biochemistry / vol. 112, Issue 11, Jun. 17, 2011. 4 pages.

Liu, Yanyan; et al. "Inhibition of thrombin by functionalized C nanoparticles revealed via in vitro assays and in silico studies," J Environ Sci (China) Jan. 2018;63:285-295. doi: 10.1016/j.jes.2017.08.013. Epub Aug. 30, 2017. 2 pages.

Vandhana Muralidharan-Chari; et al. "Thymoquinone Modulates Blood Coagulation in Vitro via Its Effects on Inflammatory and Coagulation Pathways," The Pharmaceutical Research Institute, Albany College of Pharmacy and Health Sciences, 1 Discovery Drive, Rennselaer, NY, USA. 15 pages.

Syeda Tasneem Towhid; et al. "Thymoquinone-induced platelet apoptosis," Journal of Cellular Biochemistry. Jun. 17, 2011. 3 pages.

Wang, Xuejan; et al. "Severe Thrombocytopenia Associated With Black Seed Oil and Evening Primrose Oil," Internal Medicine, Thomas Jefferson University Hospital, Philadelphia, USA. 6 pages.

A. Zaoui; et al. "Acute and chronic toxicity of Nigella sativa fixed oil," Phytomedicine 9: 69-74, 2002. 6 pages.

\* cited by examiner

NUTRACEUTICAL COMPOSITIONS COMPRISING C60 AND COX-2 INHIBITOR

FIELD OF THE INVENTION

The field of the invention is production of nutraceutical compositions.

BACKGROUND

The following description includes information that may be useful in understanding the present invention. It is not an admission that any of the information provided herein is prior art or relevant to the presently claimed invention, or that any publication specifically or implicitly referenced is prior art.

The human body is under constant attack from oxidative stress caused by free radicals from e.g., reactive oxygen species (ROS). Oxidative stress causes damage to cells, especially cellular protein and DNA, and is associated with many human diseases, including cancer, atherosclerosis, Alzheimer's disease, and Parkinson's disease. Oxidative stress also contributes to aging, which can be defined as a gradual accumulation of free-radical damage.

Buckminsterfullerene is a fullerene with the formula C60. It has a cage-like fused-ring structure (truncated icosahedron) that resembles a soccer ball, made of twenty hexagons and twelve pentagons, with a carbon atom at each vertex of each polygon and a bond along each polygon edge. Due to its 30 carbon double bonds, 60-carbon fullerene is a powerful and recyclable antioxidant that neutralizes harmful free radicals. It is reported to be 172 times more potent than Vitamin C, working as an electron reservoir to defuse reactive oxygen species (ROS) in the body, without altering its own structure.

A novel mechanism of antioxidant activity of buckminsterfullerene C60, based on protons absorbing and mild uncoupling of mitochondrial respiration and phosphorylation, was confirmed by computer modeling using Density Functional Theory. According to the model, Fullerene's geroprotective activity is significantly higher than those of the most powerful reactive oxygen species scavengers. C60 has an apparent ability to acquire positive charge by absorbing several protons, and this complex can then penetrate into mitochondria. Such a process allows for mild uncoupling of respiration and phosphorylation, which in turn leads to decrease in ROS production. See "Possible Mechanisms of Fullerene C60 Antioxidant Action," Chistyakov et al., BioMed Research International, vol. 2013, Article ID 821498, 4 pages, 2013.

Presumably due to its anti-oxidant and anti-aging properties, C60 and its derivatives have been shown to prolong life in a variety of species, including mice (Quick et al., "A carboxy-fullerene SOD mimetic improves cognition and extends the lifespan of mice" Neurobiology of Aging 29 (2008) 117-128) and rats (Baati et al., "The prolongation of the lifespan of rats by repeated oral administration of [60] fullerene," Biomaterials 33 (2012) 4936-4946). C60 fullerene was also shown to inhibit tumor growth and metastasis. See Prylutska et al., Pristine C60 Fullerenes Inhibit the Rate of Tumor Growth and Metastasis. Exp Oncol 2011, 33, 3, 162-164.

Cyclooxygenase-2 (i.e., COX-2), is an enzyme that is involved in the conversion of arachidonic acid (AA) to prostaglandin. Prostaglandin levels are increased by COX-2 during inflammation and growth, and COX-2 inhibitors can reduce the production of prostaglandins that promote inflammation. Moreover, the expression of COX-2 is up-regulated in many cancers, so inhibiting COX-2 may have anti-cancer properties. Thus, COX-2 inhibitors are thought to be beneficial in promoting health, at least in term of reducing inflammation, and treating or preventing at least some types of cancer.

Previous work has used C60 or its derivatives for health benefits. For example, U.S. Patent Application Publication No.: US 2014/0140985, and PCT publication WO 2013/025180, both by Moussa et al., teach using fullerene partially dissolved in a lipid carrier to prolong the life span in rats. U.S. Patent Application Publication No.: US 2003/0162837, by Dugan et al., teaches increasing a meta Zoan's lifespan by administering a carboxylated derivative of a C60 fullerene. U.S. Pat. No. 6,777,445 to Lei et al. teaches using fullerene to treat certain bacterial and viral infections. U.S. Pat. No. 7,163,956 to Wilson et al. teaches using substituted fullerene composition as antioxidants. However, none of these references teach the combined use of C60 and a COX-2 inhibitor.

Thus, there is a need for an improved formulation of fullerene that addresses both inflammation and oxidative stress.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

DETAILED DESCRIPTION OF THE INVENTION

The inventive subject matter provides apparatus, systems and methods in which a C60, a COX-2 inhibitor, and a medium chain triglyceride are combined to form an anti-inflammatory and anti-oxidative nutraceutical composition that confers health benefits.

In preferred embodiments, the nutraceutical composition includes one or more types of medium chain triglyceride that can at least partially act as a carrier for both C60 and a COX-2 inhibitor. Medium chain triglycerides are triglycerides with two or three fatty acids having an aliphatic tail of 6-12 carbon atoms. Those medium chain triglycerides with fatty acids having an aliphatic tail of 8 carbon atoms are preferred in the current inventive subject matter. Contemplated sources of the medium chain triglyceride include one or more of olive oil, black seed oil, corn oil, soy oil, coconut oil, avocado oil, or other vegetable oil. Oils derived from an animal can also be used, for example, fish oil. In especially preferred embodiments, the nutraceutical composition contains an emulsifier. A plant base emulsifier is preferred, for example, lecithin. It is contemplated that sunflower seed can be the source of lecithin.

Contemplated inventive nutraceutical compositions also include a COX-2 inhibitor. Preferably, the COX-2 inhibitor is COX-2 specific (as opposed to be being a COX-2 and COX-1 inhibitor) and has an IC50 less than 0.5 µM. The COX-2 inhibitor can be synthesized, but is preferably derived from a natural source (e.g., a plant product). Synthesized COX-2 inhibitors include rofecoxib (Vioxx™) and valdecoxib (Bextra™), but preferably Celecoxib (Celebrex™) Plant derived COX-2 inhibitors include thymoquinone, dithymoquinone, or thymohydroquinone, preferably derived from *Nigella sativa* (also known as "black seed"). In especially preferred embodiments, black seed oil is advantageously used to provide both medium chain triglycerides and COX-2 inhibitors.

The ratio between the C60, COX-2 inhibitor, and medium chain triglyceride in the nutraceutical composition can be any suitable value. Preferably, 1 g C60 is dissolved in 200-300 ml medium chain triglyceride. More preferably, 1 g C60 is dissolved in 240-280 ml medium chain triglyceride. The C60 used in the inventive subject matter is at least 99.9% pure. COX-2 inhibitor (e.g., thymoquinone) is preferably between 0.5-2.5% wt of the nutraceutical composition, more preferably between 1.0 and 2.0% wt. Anecdotal evidence from human volunteers has demonstrated that the combined use of C60 (antioxidant) and a COX-2 inhibitor (anti-inflammatory) has unexpected benefits in promoting health, including synergistic effects in slowing aging, and in some cases, reversing aging.

The inventive subject matter also provides a method of improving the health of a human by administering a therapeutically effective amount of the nutraceutical composition. Contemplated health benefits include improving longevity, protecting against free radicals, preventing and reducing inflammation, killing viruses, bacteria, fungus, and parasites, protecting nerves, preventing osteoarthritis, improving obesity and metabolic syndrome, preventing UV damage, stopping tremor, improving memory, increasing energy, lessening anxiety, improving focus, reducing wrinkles, and promoting a more youthful appearance.

In preferred embodiments, a person takes 3-6 dropper draws 2 times daily. Once C-60 is saturated in the body (homeostasis) one can reduce the amount taken to just 1 teaspoon a day for maintenance. Some individuals have sensitive digestive systems and too much of an oil (olive, coconut, avocado, or especially black seed oil) can incur diarrhea. In such cases the individual should back off the quantity actively taking or change to a different oil. As used herein, a teaspoon is approximately 5 droppers full, or 5 ml. If working on a health issue, it is recommended that a person continue taking the C60 twice a day, and maybe more until a difference is noticed. It is further contemplated that the nutraceutical composition can be used on pets or other animals.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

Unless the context dictates the contrary, all ranges set forth herein should be interpreted as being inclusive of their endpoints, and open-ended ranges should be interpreted to include only commercially practical values. Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A nutraceutical composition, comprising:
C60;
black seed oil;
a Cox-2 inhibitor from a source other than the black seed oil; and
a medium chain triglyceride from a source other than the black seed oil.

2. The nutraceutical composition in claim 1, wherein the nutraceutical composition comprises dithymoquinone.

3. The nutraceutical composition in claim 1, wherein the nutraceutical composition comprises thymohydroquinone.

4. The nutraceutical composition in claim 1, further comprising an emulsifier.

5. The nutraceutical composition in claim 4, wherein the emulsifier is a lecithin.

6. The nutraceutical composition in claim 5, further comprising using sunflower seed as the source of the lecithin.

7. The nutraceutical composition in claim 1, further comprising a COX-1 inhibitor.

8. The nutraceutical composition of claim 1, wherein the medium chain triglyceride is selected from the list consisting of olive oil, corn oil, soy oil, coconut oil, and avocado oil.

9. A nutraceutical composition, wherein active ingredients consist essentially of C60; black seed oil; and a Cox-2 inhibitor from a source other than the black seed oil.

10. A nutraceutical composition, wherein active ingredients consist of C60, black seed oil; and a Cox-2 inhibitor from a source other than the black seed oil.

11. A method of improving health in a mammal, comprising administering a therapeutically effective amount of the nutraceutical composition in claim 1.

* * * * *